United States Patent
Garino

(10) Patent No.: US 10,258,476 B2
(45) Date of Patent: Apr. 16, 2019

(54) CRUCIATE REPLACING ARTIFICIAL KNEE

(71) Applicant: Jonathan P. Garino, Villanova, PA (US)

(72) Inventor: Jonathan P. Garino, Villanova, PA (US)

( * ) Notice: Subject to any disclaimer, the term of this patent is extended or adjusted under 35 U.S.C. 154(b) by 0 days.

(21) Appl. No.: 14/960,861

(22) PCT Filed: Nov. 24, 2015

(86) PCT No.: PCT/US2015/062386
§ 371 (c)(1),
(2) Date: Dec. 7, 2015

(87) PCT Pub. No.: WO2016/085963
PCT Pub. Date: Jun. 2, 2016

(65) Prior Publication Data
US 2017/0252173 A1    Sep. 7, 2017

Related U.S. Application Data

(60) Provisional application No. 62/084,017, filed on Nov. 25, 2014.

(51) Int. Cl.
*A61F 2/08* (2006.01)
*A61F 2/38* (2006.01)
*A61F 2/30* (2006.01)

(52) U.S. Cl.
CPC ............ *A61F 2/3836* (2013.01); *A61F 2/389* (2013.01); *A61F 2/3859* (2013.01);
(Continued)

(58) Field of Classification Search
CPC .......... A61F 2/3859; A61F 2/389; A61F 2/38; A61F 2/3886; A61F 2/3868;
(Continued)

(56) References Cited

U.S. PATENT DOCUMENTS

| | | |
|---|---|---|
| 3,945,053 A | 3/1976 | Hillberry et al. |
| 4,597,766 A | 7/1986 | Hilal et al. |

(Continued)

FOREIGN PATENT DOCUMENTS

| | | |
|---|---|---|
| DE | 3333815 A1 | 4/1985 |
| DE | 3742695 A1 | 6/1989 |

(Continued)

OTHER PUBLICATIONS

International Preliminary Report of Patentability and Written Opinion for International Application No. PCT/US2015/062386, dated May 30, 2017—8 Pages.

(Continued)

*Primary Examiner* — Ann Schillinger
(74) *Attorney, Agent, or Firm* — RatnerPrestia

(57) ABSTRACT

A prosthetic knee with an artificial ACL/PCL. The prosthetic knee includes a femoral component and a tibial component. The artificial ACL/PCL connects the femoral component and the tibial component and includes an anterior cruciate ligament portion connecting an anterior anchor point on the tibial component to a posterior anchor point on the femoral component, and a posterior cruciate ligament portion connecting a posterior anchor point on the tibial component to an anterior anchor point on the femoral component. The artificial ligament may be provided as single length of material and may be pre-assembled into an ACL/PCL module having portions that may be inserted into at least one of the femoral component or the tibial component. A system is also provided for total knee replacement that includes a selection of femoral components, tibial components, and one or more ACL/PCL modules of varying sizes.

15 Claims, 12 Drawing Sheets

(52) U.S. Cl.
CPC .................. *A61F 2002/305* (2013.01); *A61F 2002/30462* (2013.01); *A61F 2002/30479* (2013.01)

(58) Field of Classification Search
CPC ............ A61F 2002/30604; A61F 2/461; A61F 2002/3863; A61F 2002/4205
See application file for complete search history.

(56) References Cited

U.S. PATENT DOCUMENTS

| | | | |
|---|---|---|---|
| 4,770,663 A | 9/1988 | Hanslik et al. | |
| 5,425,733 A | 6/1995 | Schmieding | |
| 5,935,133 A | 8/1999 | Wagner et al. | |
| 6,325,804 B1 * | 12/2001 | Wenstrom, Jr. .... | A61B 17/0401 606/331 |
| 6,905,513 B1 | 6/2005 | Metzger | |
| 7,153,327 B1 | 12/2006 | Metzger | |
| 8,343,227 B2 | 1/2013 | Metzger et al. | |
| 9,011,547 B2 | 4/2015 | Auger et al. | |
| 2009/0210066 A1 | 8/2009 | Jasty | |
| 2010/0191342 A1 * | 7/2010 | Byrd ........................ | A61F 2/08 623/20.28 |
| 2010/0324676 A1 * | 12/2010 | Albertorio ......... | A61B 17/0401 623/13.14 |
| 2012/0130492 A1 | 5/2012 | Eggli et al. | |
| 2013/0096679 A1 | 4/2013 | Laurencin et al. | |
| 2013/0173010 A1 | 7/2013 | Irwin et al. | |
| 2013/0297020 A1 | 11/2013 | Wolfson et al. | |
| 2014/0094912 A1 | 4/2014 | Walker | |
| 2014/0105951 A1 | 4/2014 | Altman et al. | |

FOREIGN PATENT DOCUMENTS

| | | |
|---|---|---|
| FR | 2634373 A1 | 1/1990 |
| JP | 2011147779 A | 8/2011 |
| JP | 2014087706 A | 5/2014 |
| WO | 8707135 A1 | 12/1987 |
| WO | 2005002473 A1 | 1/2005 |
| WO | WO 2012/100962 A1 | 8/2012 |

OTHER PUBLICATIONS

Cooper et al., "Fiber-Based Tissue-Engineered Scaffold for Ligament Replacement: Design Considerations and In Vitro Evaluation", Biomaterials, vol. 26, 2005, pp. 1523-1532.

Legnani et al., "Anterior Cruciate Ligament Reconstruction With Synthetic Grafts. A Review of Literature", Int. Orthop, 2010, vol. 34, No. 4, 12 pages.

International Search Report for PCT Application No. PCT/US2015/062386 dated Feb. 1, 2016.

Notification of Reasons for Rejection for Japanese Application No. 2017-527275, dated Jun. 26, 2018, with translation, 11 pages.

* cited by examiner

CRUCIATE REPLACING ARTIFICIAL KNEE

CROSS REFERENCE TO RELATED APPLICATION

This application claims the benefit of PCT International Application No. PCT/US2015/062386, filed Nov. 24, 2015 claiming the benefit of U.S. Provisional Application No. 62/084,017 filed on Nov. 25, 2014, the contents of which are incorporated herein by reference in their entirety.

FIELD OF THE INVENTION

This invention relates generally to artificial knee prostheses used for Total Knee Replacement (TKR), and more particularly, to a knee joint prosthesis having a more anatomically accurate artificial anterior cruciate ligament (ACL) and/or posterior cruciate ligament (PCL).

BACKGROUND OF THE INVENTION

Prosthetic knees generally include three main components, a femoral component (FIGS. 1A and 1B), which is attached to the distal end of the femur, a tibial component (FIGS. 2A and 2B), which is implanted onto the proximal end of the tibia, and an articular insert (FIGS. 3A and 3B), which is mounted onto the tibial component and provides a frictional surface for the femoral component. The components are designed to simulate a joint and the associated mechanics of a human knee throughout the knee's range of motion. The components are generally provided in a variety of shapes with varying dimensions (identified as dimensions A-H and J-T in FIGS. 1A to 3B), so that a physician is able to select the optimal combination of components depending on the specific anatomy of the patient. The size and shape of the knee is dependent on various factors including age, gender, and size of the patient. Therefore, a fairly large inventory of components are generally made available, so that the prosthetic knee may be tailored for the patient, During the course of a routine knee construction with a TKR, the ACL is removed in a vast majority of all cases and depending on the selected TKR design, the patient's PCL is either retained or substituted with some mechanism to replace the lost function of the PCL. Even when the PCL is retained, often a portion of the PCL must be cut or partially cut during surgery to aid in the balancing of the knee replacement. When the PCL is completely removed, the PCL is substituted by a post and cam mechanism.

Referring to FIGS. 1A, 1B, 3A, and 3B, an illustration of a typical design of a post and cam mechanism is provided. An articular insert 22 includes an extension 24 that protrudes into an opening 12 of the femoral component 10. The extension 24 includes a posterior surface 25 that is intended to be in frictional contact with the posterior surface 14 of the opening 12 when the joint is flexed. The resistance generated when the extension 24 bears against the posterior surface 14 of the opening 12 in the femoral component 10 is intended to simulate the resistance that would have been generated by a healthy posterior cruciate ligament (PCL). Cam and post mechanisms have been manufactured that partially replace the function of an ACL by creating a cam surface between the anterior surface of the extension 24 and the anterior surface of the opening 12; however, this solution provides only a partial substitution of an ACL because the anterior side of the extension 24 is at best able to contact the anterior side of the opening only between 0 to 20 degrees of flexion.

Another solution is to connect the femoral component and tibial component with a cable-like material, such as the material disclosed in U.S. Pat. No. 5,935,133, the contents of which are incorporated herein by reference. But this artificial material is typically only used to replace the PCL and not the ACL.

These common solutions are deficient in that a replacement has not been provided to generate resistance simulating an ACL. Essentially, the ACL is sacrificed. The lack of an anatomically correct replacement may result in a TKR having reduced functionality compared to the original knee. This may create difficulties during physical therapy following surgery, as well as limit the patient's ability or desire to participate in physical activity following therapy. Virtually all modern total knee replacements sacrifice the ACL or inadequately substitute it with a crude cam and post mechanism, thus leaving the reconstructed knee with kinematics similar to that of an ACL-deficient knee. Normal knee kinematics therefore remain elusive. In addition, the lack of proper interplay between an ACL and PCL (which together drive normal knee kinematics) leaves the TKR reconstruction short of producing a relatively normal knee for the patient.

Given the complexity of the mechanics of a knee joint and the difficulty for patients to adjust to an artificial knee after surgery, an anatomically correct knee replacement system is needed that more accurately simulates the resilience and support formerly provided by the removed ligaments.

SUMMARY OF THE INVENTION

In one embodiment of the present invention, a prosthetic knee is provided that comprises a femoral component, a tibial component, and at least one artificial ligament connecting the femoral component and the tibial component, the at least one artificial ligament comprising an anterior cruciate ligament portion connecting an anterior anchor point on the tibial component to a posterior anchor point on the femoral component, and a posterior cruciate ligament portion connecting a posterior anchor point on the tibial component to an anterior anchor point on the femoral component. The tibial component comprises an articular insert configured to be coupled to the tibial component and the at least one artificial ligament comprises a single length of material in which the anterior cruciate ligament portion and the posterior cruciate ligament are connected to one another. In another embodiment, the anterior cruciate ligament portion and the posterior cruciate ligament portion may be discrete components that are not connected to one another.

In another embodiment of the present invention, an ACL/PCL module is provided. The module may be attachable to a prosthetic knee having a femoral component, an articular insert, and a tibial component and may comprise at least one of a femoral portion configured to be coupled to the femoral component and a tibial portion configured to be coupled to at least one of the articular insert and the tibial component and at least one artificial ligament connecting the femoral component and the tibial component. The at least one artificial ligament comprises an anterior cruciate ligament portion connecting an anterior anchor point on the tibial portion or tibial component to a posterior anchor point on the femoral portion or femoral component, and a posterior cruciate ligament portion connecting a posterior anchor point on the tibial portion or tibial component to an anterior anchor point on the femoral portion or femoral component. The at least one artificial ligament may comprise a single length of material in which the anterior cruciate ligament portion and the posterior cruciate ligament are connected to one another, or the anterior cruciate ligament portion and the posterior cruciate ligament portion may be discrete components that are not connected to one another.

In yet another embodiment of the present invention, a system for providing total knee replacement on a plurality of patients of different sizes is provided. The system may comprise a plurality of femoral components, a plurality of tibial components, a plurality of articular inserts, and at least one ACL/PCL module. The plurality of femoral components comprise a plurality of differently sized femoral components each configured to accommodate a range of patient femoral anatomies. The plurality of tibial components comprise a plurality of differently sized tibial components each configured to accommodate range of patient tibial anatomies. Each articular insert is configured for installation between the distal portion of the femur on which one of the plurality of femoral components is fixed and the proximal portion of the tibia on which one of the plurality of tibial components is fixed. The ACL/PCL module comprises at least one of a femoral portion configured to be coupled to one or more of the femoral components and a tibial portion configured to be coupled to one or more of the tibial components or one or more of the articular inserts, and at least one artificial ligament connecting the femoral component and the tibial component. The at least one artificial ligament comprising an anterior cruciate ligament portion connecting an anterior anchor point on the tibial portion or the tibial component to a posterior anchor point on the femoral portion or the femoral component, and a posterior cruciate ligament portion connecting a posterior anchor point on the tibial portion or tibial component to an anterior anchor point on the femoral portion or the femoral component.

DETAILED DESCRIPTION

Figure 4:
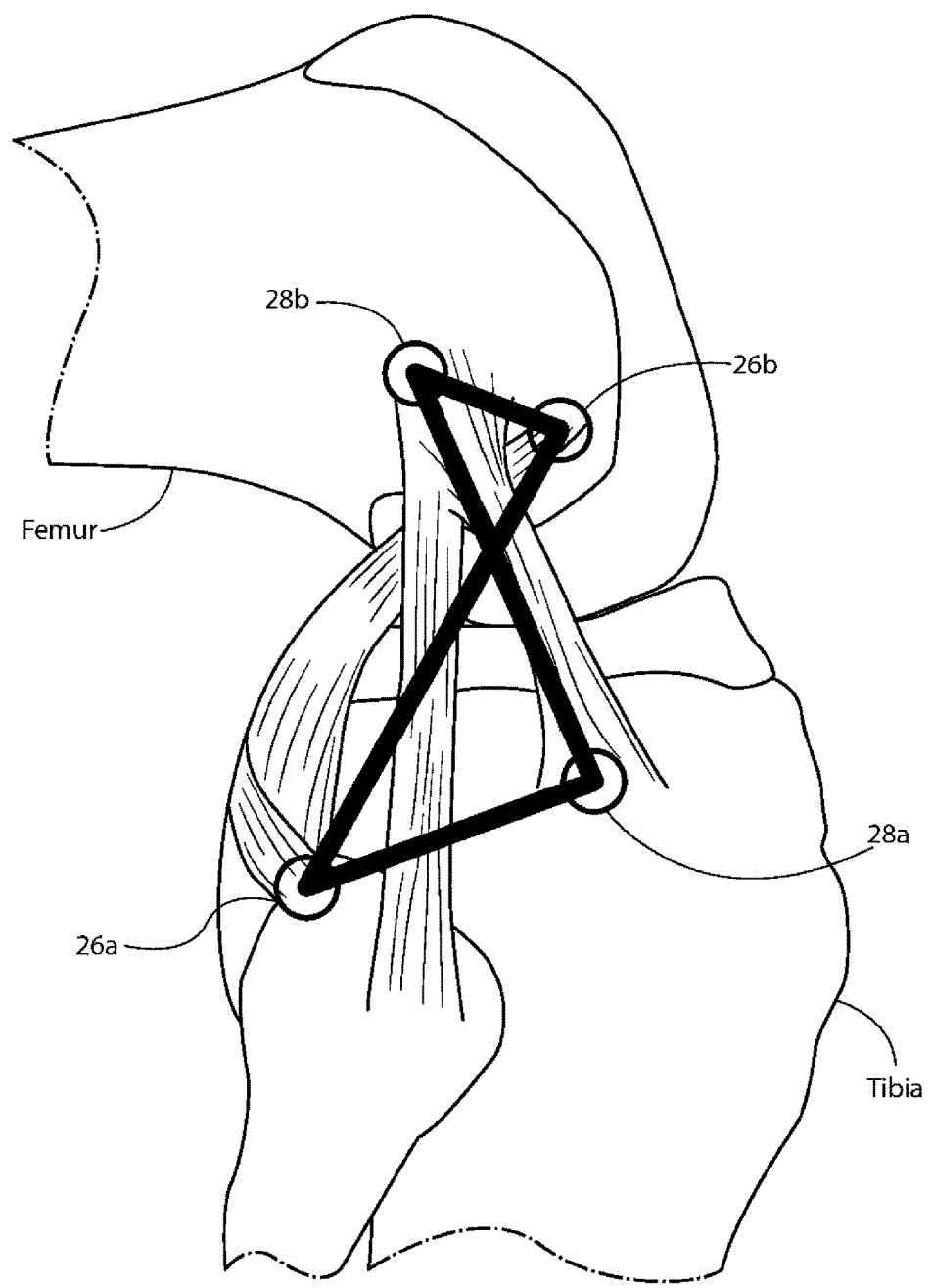
FIG. 4 is a side view of a knee joint illustrating the anatomical location of the ACL and PCL and the configuration of an artificial material intended to replace the ACL and PCL according to one embodiment of the present invention.

In order to provide a more anatomically correct TKR, prosthesis embodiments that replicate the function provided by both the ACL and PCL are desirable. Referring to FIG. 4, a healthy human knee is illustrated with a loop 30, representing an exemplary artificial ACL/PCL ligament, drawn over the location of the original anatomical ACL and PCL. The section of the loop 30 constituting the artificial PCL is bounded by points 26A and 26B. The section of the loop 30 constituting the artificial ACL is bounded by points 28A and 28B.

Generally, the present invention provides various methods of utilizing an artificial material, preferably a synthetic fiber or cord, to replace an ACL and PCL, such that the artificial material is configured similarly to the respective orientation and location of the ACL and PCL in a normal knee. It should be understood, however, that the term "artificial" means only that it is not the original anatomical ACL or PCL ligament in its original form prior to the TKR, and should not be interpreted as a limitation to the use of only synthetic materials. Accordingly, the artificial ligament, may comprise "natural" materials, such as materials fashioned from biologically created materials and/or may comprise a hybrid of synthetic and natural materials. Specifically, the configuration is such that the origin and insertion points of the artificial material in a TKR is similar to the origin and insertion points of the ACL and PCL in a normal knee.

For example, according to various embodiments of the present invention, the artificial material in the form, for example, of artificial ligament may be incorporated into the TKR either at the time of surgery or the TKR may be pre-assembled with the artificial material in advance of surgery. At the time of the surgical procedure, the surgeon may use either a single strand of artificial ligament that is woven between the femoral component and articular insert with attachment points on either the femoral component or the articular insert of the TKR, or the surgeon may use two lengths of artificial material, one for the ACL and the other for the PCL. Alternatively, the TKR may be preassembled in a similar fashion in advance of surgery.

Once the artificial material is in place, metallic pieces may be used to crimp and permanently grip the ends. These metal pieces, however then preferably lock into the appropriate anatomical end points of an ACL and PCL in a manner such that the ends of the artificial material do not move or fret. Alternatively the ends of the artificial material may be brought in proximity of one another and tied or sewn together into a continuous loop. In another embodiment, smooth round metal balls may be used to crimp the artificial material and anchor the ends of the artificial material into the articular insert. The round shape of the balls allows the artificial material to move very slightly, reducing stress at the attachment point. Using a spherical anchor that has a diameter larger than the diameter of the artificial material and the diameter of the exit hole in the articular insert may also reduce impingement and stress at these points. It is preferable to include a smooth tunnel in the articular insert, tibial component, and/or femoral component through which the artificial material may be inserted, with the ends of the tunnel located in the approximately correct anatomical location of the endpoints of the ACL and PCL in the knee. Preferably, the opening of each side of the tunnel is also smooth. A smooth tunnel may protect the artificial material from the bone and prevent other potential problems, such as impingement and fretting of the artificial material during movement of the TKR.

In one method according to the present invention, the artificial material, such as an artificial ligament, may be provided separately from the TKR. During the replacement procedure, the surgeon may weave the ligament through the femoral component and articular insert and fasten the ends. Care should be taken when using this method in order to limit the potential error that may result, for example, from inadequate fastening or leaving an inappropriate length of artificial ligament when fastening is completed.

In another embodiment of the present invention, a single strand of artificial ligament may be weaved through a channel in the femoral component of a TKR and the ends of the artificial ligament may be attached to a tibial insert that locks into the tibial baseplate. The articular insert may then be provided with cut-outs to allow passage of the artificial ligament to the femoral component from the tibial insert. The femoral component of the TKR of this embodiment may be pre-assembled with the artificial ligament and the tibial insert. The tibial insert may be standardized to fit into any size tibial component of a TKR. However, the length of the artificial ligament may be variable to accommodate different size femoral components and articular inserts.

Alternatively, the artificial material may be attached to the articular insert, such that the articular insert, artificial material, and the femoral component are pre-assembled together. During the TKR after the femoral component and the tibial component are in place, the articular insert may be snapped onto the tibial component in typical fashion. However, because articular inserts and femoral components are provided in different sizes, multiple combinations of the femoral components and articular inserts may result in a large inventory of different pre-assemblies.

In yet another embodiment, one or more artificial ligaments may be woven through and/or the ends anchored to one or more modular inserts. The modular inserts may be inserted into one or more of the femoral component, tibial component, and articular insert of the TKR.

Figure 5:
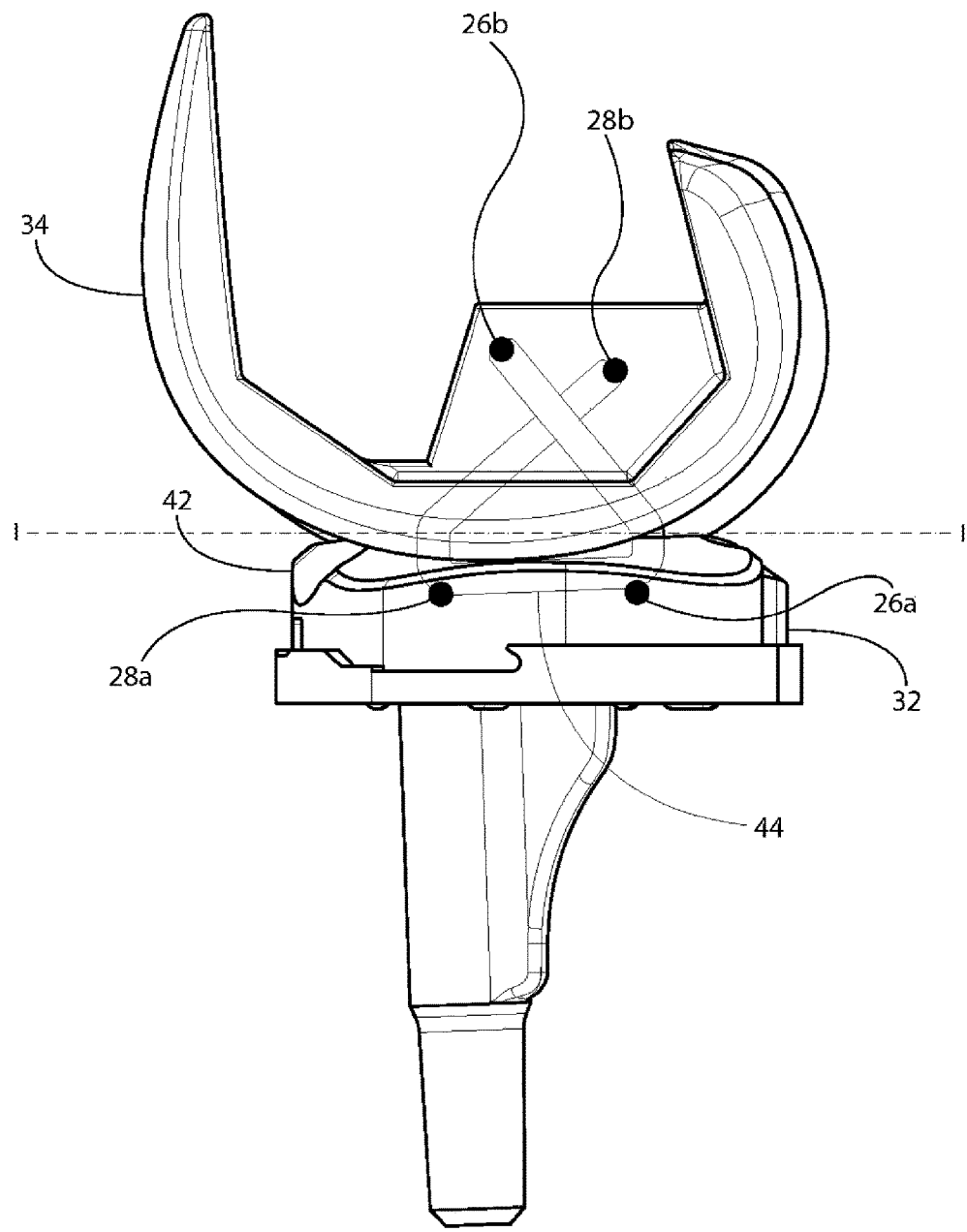
FIG. 5 is a side view of a femoral component, articular insert, and artificial ligament for a TKR according to another embodiment of the present invention.
Figure 6A:
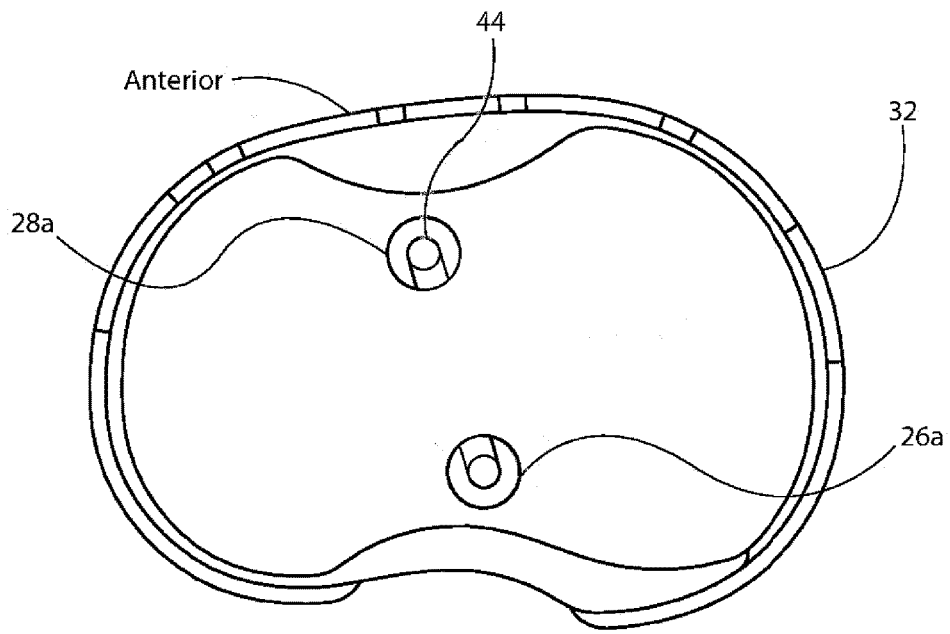
FIG. 6A is a top view of a cross-section along line I-I of FIG. 5.
Figure 6B:
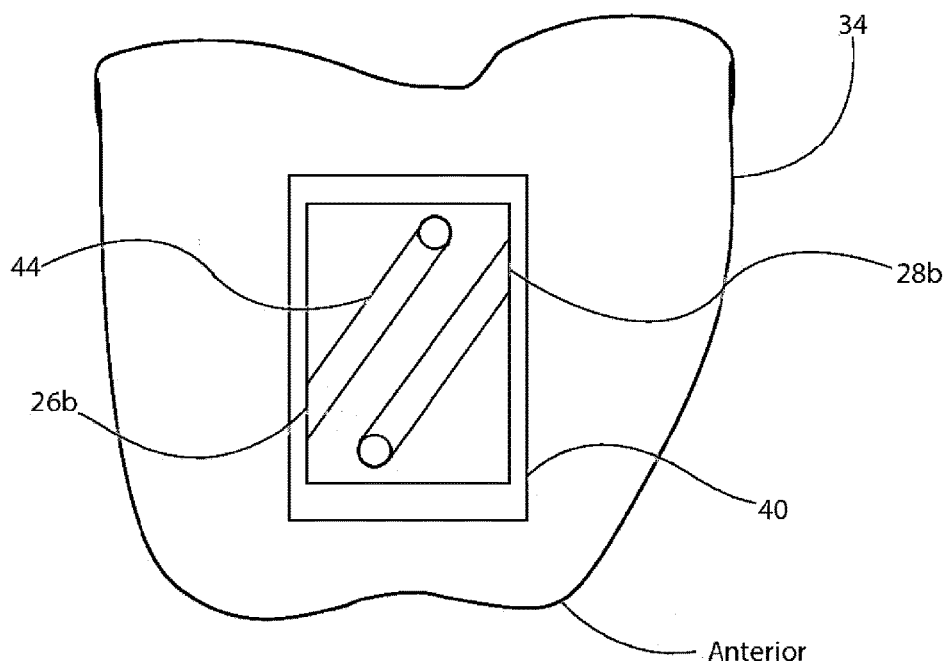
FIG. 6B is a bottom view of a cross-section along line I-I of FIG. 5.

Referring now to FIGS. 5, 6A, and 6B illustrating a first embodiment of the present invention, the connection points 26a, 26b, 28a, and 28b of the artificial material, provided as ligament 44, and the lengths spanning between the connection points, provided as an outline of the artificial ligament 44, are configured to simulate the dimensions and attachment points of the ACL and PCL in a human knee, as illustrated in FIG. 4. At least one length of artificial ligament, such as for example the material disclosed in U.S. Pat. No. 5,935,133, may be provided to connect the articular insert and femoral component of a TKR. The ligaments may be strung during surgery and fastened.

In a preferred embodiment, the artificial ligaments comprise a cord-like material. Preferred ligament materials are non-elastic or minimally elastic, similar to a natural ligament. Exemplary materials may comprise a variant of a woven polyethylene similar to material previously marketed as SecureStrand® cable, a braided, ultra high molecular weight polyethylene (UHMWPE) cable used for surgical fixation in posterior spinal reconstruction, material currently marketed as Super Cables® (Kinamed, Inc., Camarillo, Calif.) made from UHMWPE and Nylon 6/6,6, Gore-tex® (PTFE fiber manufactured by W. L. Gore and Associates, Inc. Newark, Del.), carbon fiber, or other similar woven materials.

In one embodiment, the artificial ligament 44 comprises a single length of material that weaves between the femoral component 34 and articular insert 32. For example referring to FIGS. 5, 6A, and 6B, a single length of artificial ligament may extend from a first end disposed adjacent an upper inner surface of femoral component 34 at an attachment point 26b in the femoral component 34 to and through the top surface of the articular insert 32 through opening 26a, The underside of the articular insert 32 may have a groove (not shown) or a bore within the thickness of the insert 32 to define a path between openings 26a and 28a to receive ligament 44, which then extends from the underside of articular insert 32 through opening 28a to an attachment point 28b in the femoral component 34, such that the second end of the ligament 44 is also disposed on the upper inner surface of the femoral component. The ends of the artificial ligament 44 may be fastened to the femoral component using any fastening means known in the art, such as but not limited to a clip or a knot. Alternatively, each end of the artificial ligament 30 may define a loop, and the fastening means may include a hook on a surface of the femoral component 34 or one or more fasteners, such as a screw or nail inserted through the loops and into the femoral or tibial component. Alternatively, the ends of the artificial ligament may be connected to each other to form a continuous loop.

The location of the ends and the order in which artificial ligament 44 weaves among points 26a, 26b, 28a, and 28b is not limited to any particular configuration, as long as the ACL/PCL structure creates at least one connection between openings 26a and 26b and at least one connection between openings 28a and 28b, as illustrated in FIG. 4. For example rather than starting at either attachment point 26b or 28b in the femoral component 34, as illustrated in FIG. 5, the starting and ending points may be 26a or 28a in the articular insert. The use of a single strand in various embodiments of the present invention is preferable because it reduces the number of parts needed to fabricate the artificial ACL/PCL of the TKR; however, two or more lengths of the artificial ligament 44 may also be used.

Referring again to FIGS. 1A to 3B, it is common for manufacturers to provide knee prostheses of varying sizes and shapes in order to accommodate different patients, For example the dimensions of the femoral component 10, tibial component 16, and articular insert 22 labeled as A to H and J to T may vary with respect to a plurality of sizes to accommodate variations in human anatomy. For example, a particular TKR system design may feature a plurality of standard size tibial components (e.g. 10, for a Journey® Knee by Smith & Nephew), a plurality of standard size femoral components (e.g. 10, for a Journey® Knee by Smith & Nephew), and a plurality of standard size articular inserts (e.g. 4, for a Journey® Knee by Smith & Nephew), forming a vast number of acceptable combinations and permutations. The physician before and during surgery typically measures and selects the correct size components to include in the TKR, based upon the size of the individual receiving the TKR and their relevant bone and joint structures. Therefore, in some embodiments, artificial ligament 44 may not be placed between the femoral component and the articular insert until after the correct size components have been selected.

Knee replacement surgery requires the use of anesthetics. In order to ensure patient safety, doctors strive to perform the TKR procedure as quickly and efficiently as possible. During the procedure, the position of the various components of the prosthetic knee joint may be manipulated on the femur and tibia until the final position is set. Accordingly, it may be preferable to avoid connecting the femoral component and articular insert with an artificial ligament until close to the end of the procedure, when the components are in place on the patient. Because it may be difficult to weave the artificial ligament between the femoral component and the articular insert after the components have been installed, another embodiment of the present invention provides a removable ACL/PCL module that is separate from the femoral component and articular insert. The ACL/PCL module may be pre-assembled and may house the artificial ligaments, such that when the femoral component and tibial component of a TKR are in place, the ACL/PCL module may then be easily inserted and fastened between the two components.

An ACL/PCL module according to various embodiments of the present invention are illustrated in FIGS. 7A-10C. The module 36 includes at least one of an upper femoral portion 40 and a lower tibial portion 42 connected by an artificial ligament 44. The artificial ligament 44 may be one or more strands, preferably a single strand woven between the two portions. For example, the artificial ligament 44 may have an end 37B that is fastened to one upper inner side of the upper femoral portion 40. The artificial ligament 44 may then extend from one side of the femoral portion 40, through the posterior part of the tibial portion 42 (substituting for the PCL), from the posterior to the anterior along the undersurface of the tibial portion 42, through the anterior of the tibial portion 42 (substituting for the ACL), and then fastened to another upper inner surface of the femoral portion 40 at end 37A. The resulting upper femoral portion 40 and lower tibial portion 42 therefore are attached to form one linked piece, for example, by one band. Other configurations for connecting artificial ligaments between the femoral and tibial portions of the module may also be used. For example, multiple artificial ligaments, such as segments 44a and 44b in FIG. 7B, may be used to connect the respective parts of the module rather than a single ligament or the starting and ending positions may differ for a single ligament configuration.

Figure 7A:
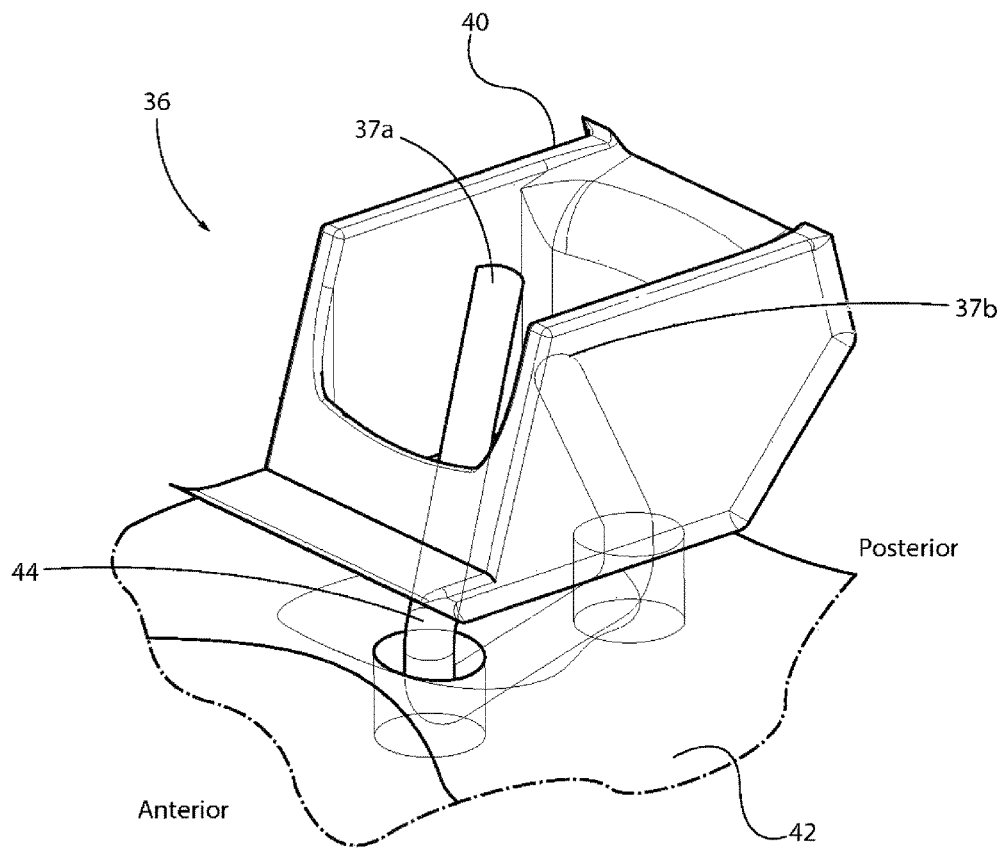
FIG. 7A is a top perspective view of an ACL/PCL module of an embodiment of the present invention.
Figure 7B:
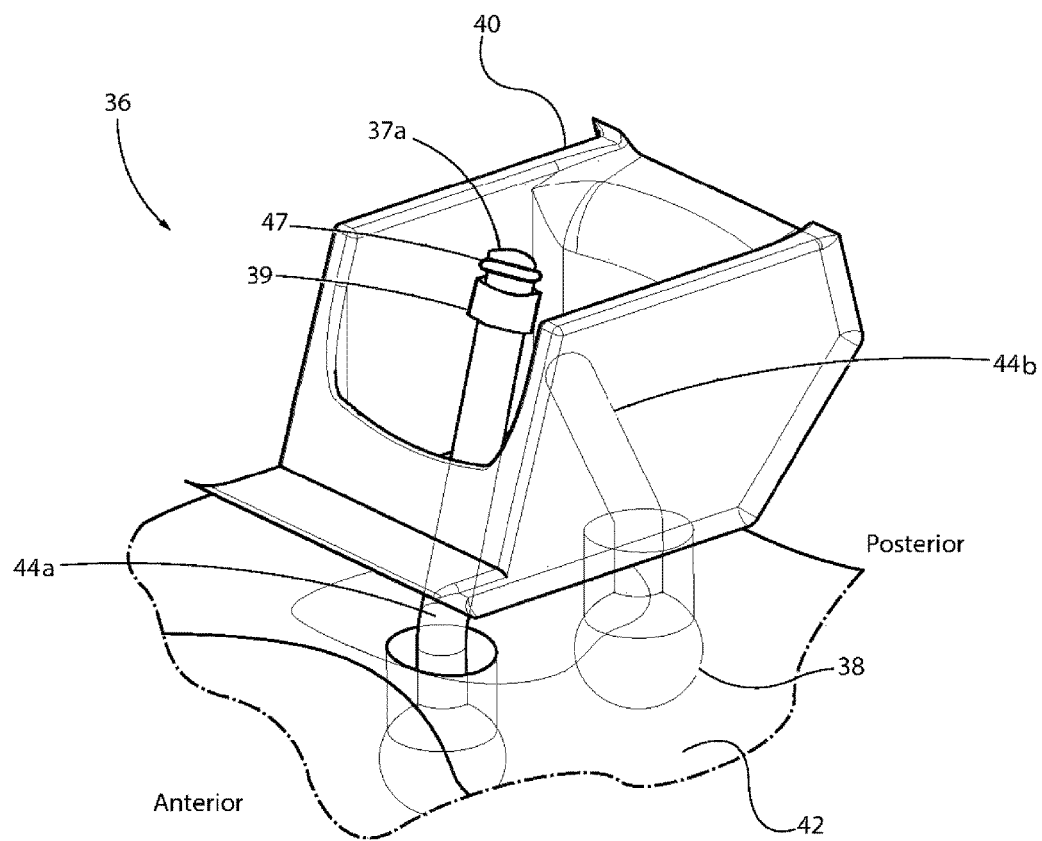
FIG. 7B is a top perspective view of an ACL/PCL module of another embodiment of the present invention.
Figure 7C:
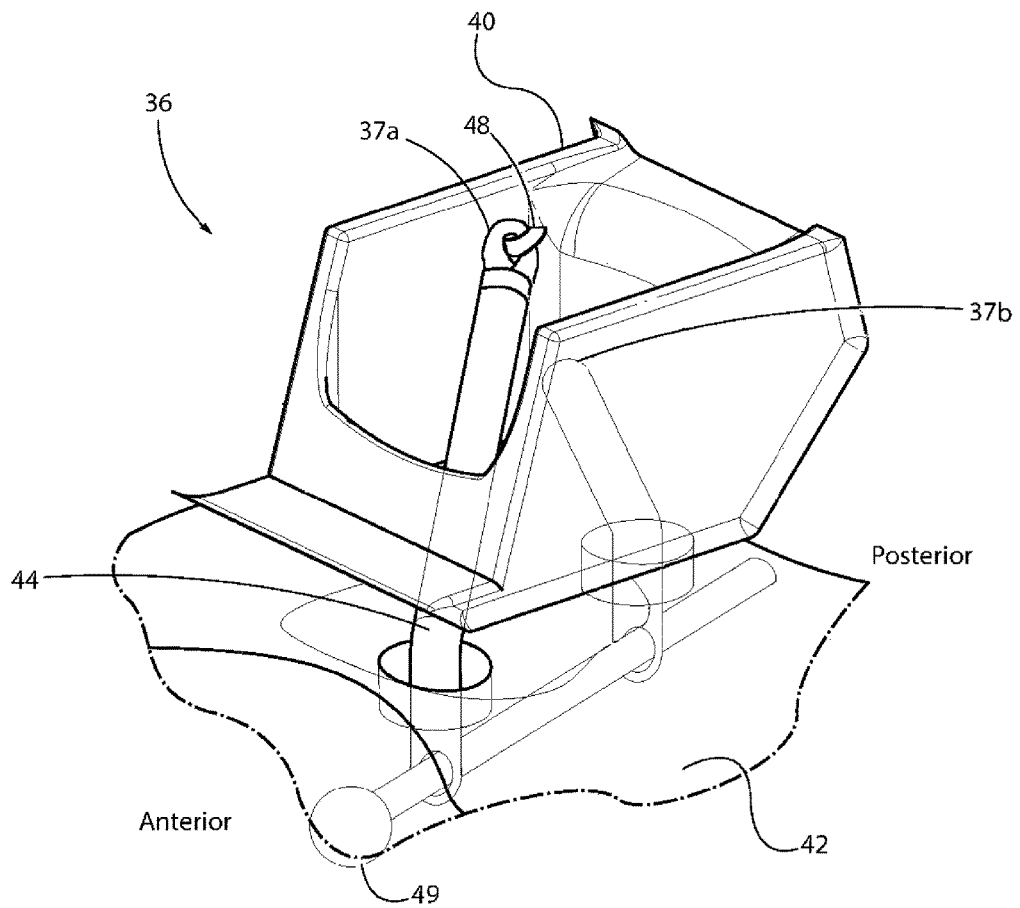
FIG. 7C is a top perspective view of an ACL/PCL module of yet another embodiment of the present invention.

The locking mechanism for the ends of the artificial ligaments are not limited to any particular construction. For example, in the embodiment illustrated in FIG. 7B, the ends of ligament sections 44a, 44b within the tibial portion 42 are anchored with a spherical retainer 38. The spherical retainer 38 preferably has a diameter which is larger than the opening in the tibial portion 42 through which the ligament sections 44a, 44b are inserted. The retainer may be applied to the ends of the ligament sections 44a, 44b by any methods known to those of skill in the art. For example, the spherical retainer 38 may be crimped onto the ends of the ligament sections 44a, 44b. Another example of a locking mechanism is illustrated at end 37a of ligament section 44a, The end 37a is attached to the femoral portion 40 by inserting the end 37a through a loop 39 attached to the upper inner surface femoral portion 40. The another type of retainer 47, such as a metal clip having a width greater than the inner dimension of the loop 39, may be attached to the end 37a to maintain the ligament section 44a within the loop 39. Alternatively, the retainer 47 may be used to join the two upper ends of the ligament sections 44a, 44b. As previously mentioned, the mechanism may also be provided in the form of a hook 48, as illustrated in FIG. 7C, and the retainer 47 may instead be used to form a loop in the end 37a of the ligament section 44a. The ligament loop may then be secured to the hook 48. Alternatively, loops present on one or both ends of the artificial ligament may be fastened to one or both of the femoral portion and tibial portion of the ACL/PCL module with a fastener, such as a nail or screw. For example, a fastener 49 in the form of a nail illustrated in FIG. 7C is inserted through loops at the ends of the artificial ligament 44 in the tibial portion 42 of the module. As would be understood by one of skill in the art, the ACL/PCL modules according to the present invention may utilize different combinations of fastening mechanisms and are not limited to the combinations illustrated in FIGS. 7A-7C.

The upper and lower portions of the ACL/PCL module may be made of the same or similar material as the femoral component, tibial component, and/or articular insert, or a different material. In general, however, all materials are preferably inert, not prone to cause infection, and otherwise safe and approved for use as a surgical implant. Exemplary materials include polyethylene, surgically approved metal alloys, surgically approved ceramic materials, or a combination thereof. Any well-known materials in the field of surgical implants may be used to fabricate any of the various embodiments or portions thereof according to the present invention.

Figure 8:
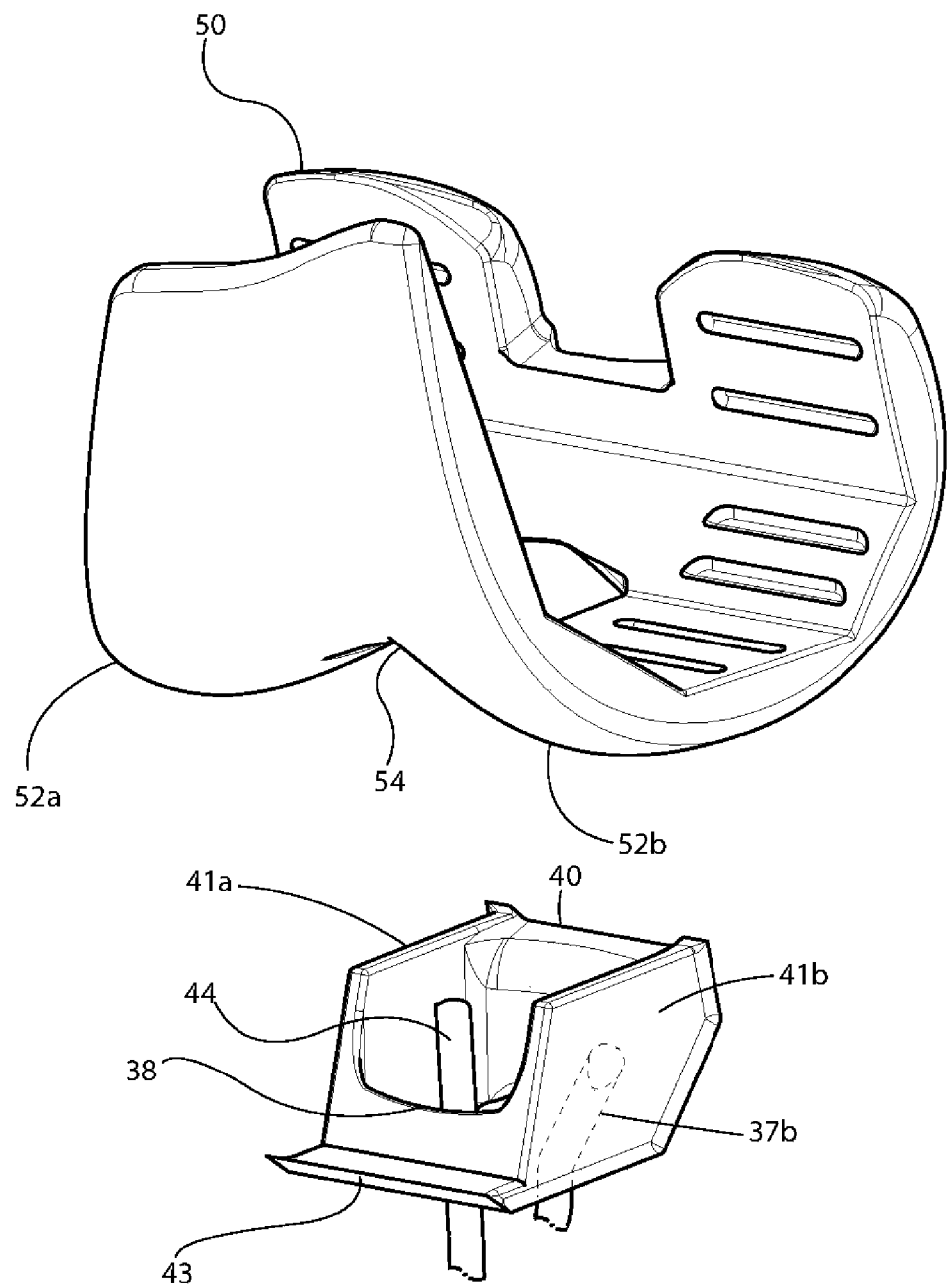
FIG. 8 is a top perspective view of the femoral portion of the embodiment illustrated in FIG. 7A with a femoral component.
Figure 9B:
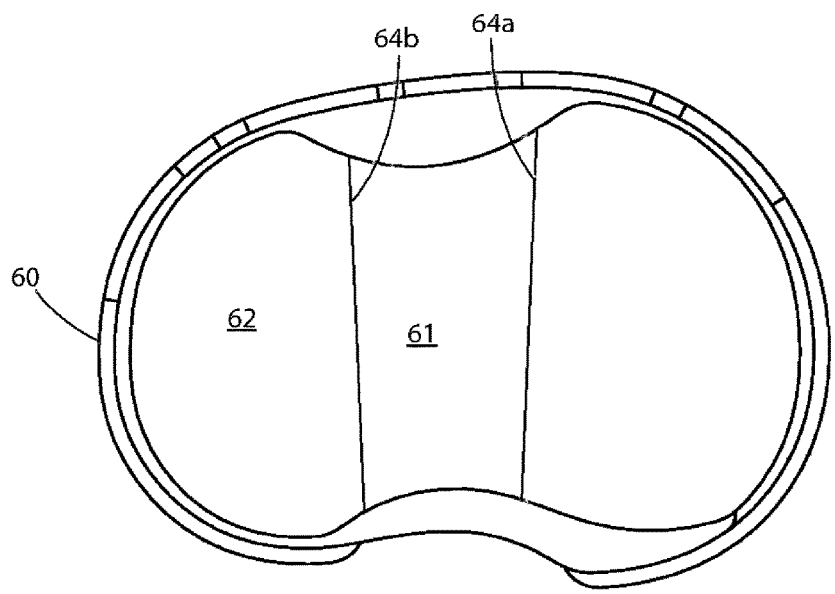
FIG. 9B is a top view of an articular insert that may be combined with the tibial portion of FIG. 9A.
Figure 9A:
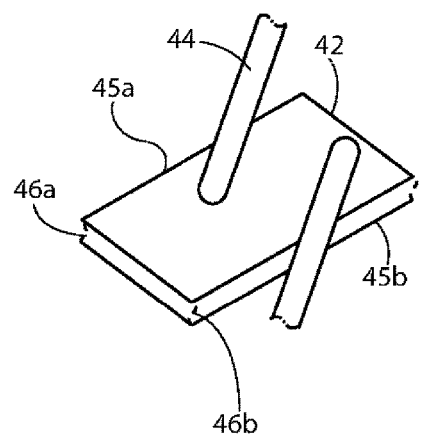
FIG. 9A is a top perspective view of a tibial portion according to another embodiment of the present invention.

One aspect of the exemplary embodiment comprising both an artificial ACL and PCL in a modular construction, is that the module may be easily and removably secured to the femoral component of a TKR. As illustrated in FIG. 8, a gap 54 may be provided in the femoral component 50 between medial 52A and lateral 52b portions intended to replicate the medial and lateral condyle and the intercondylar fossa of the femur. The width of the gap 54 may be substantially equal to the width 43 of the upper femoral portion 40 of the ACL/PCL module, to permit the attending physician to slide the module into place, such that the side walls 41A and 41b frictionally engage the medial and lateral portions 52A and 52b of the femoral component 50.

In another aspect of this exemplary embodiment, lower tibial portion 42 may be easily and removably inserted into an articular insert 60. The top surface 62 of the articular insert 60 may include a groove 61. The sides 64A, 64b of the groove 61 may optionally converge to provide a taper. The bottom tibial portion 42 of the ACL/PCL module may have side walls 45A, 45b with optional recesses 46a, 46b that mate with sides 64a, 64b of groove 61. Side walls 45a, 45b of the bottom tibial portion 42 may be parallel or converge to a lesser degree than the sides 64a, 64b of the groove 61 to secure the bottom tibial portion 42 to the articular insert 60 in a self-locking taper configuration, such as what is commonly referred to as a Morse taper. Instead of providing the groove 61 in the articular insert 60, the groove 61 may alternatively be provided in the top surface of an tibial component of a TKR, such as the tibial component 16 in FIGS. 2A and 2B; however, an articular insert used with such a modified tibial component comprises a corresponding cutout, for example, such as the articular insert 72 of FIG. 10C described in more detail below. The ligament 44 attached, embedded, and/or inserted in the tibial portion 42 illustrated in FIG. 9A may be directly connected to a femoral component of a TKR or to a femoral portion of an ACL/PCL module, such as the femoral portion 40 illustrated in FIG. 7B.

Figure 1A:
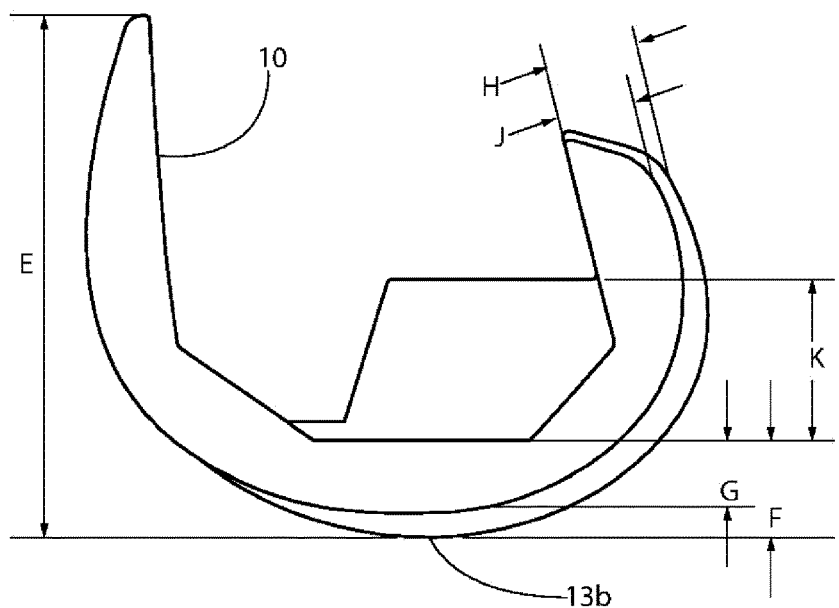
FIG. 1A is a side view of a femoral component for a knee joint prosthesis known by those of ordinary skill in the art.
Figure 1B:
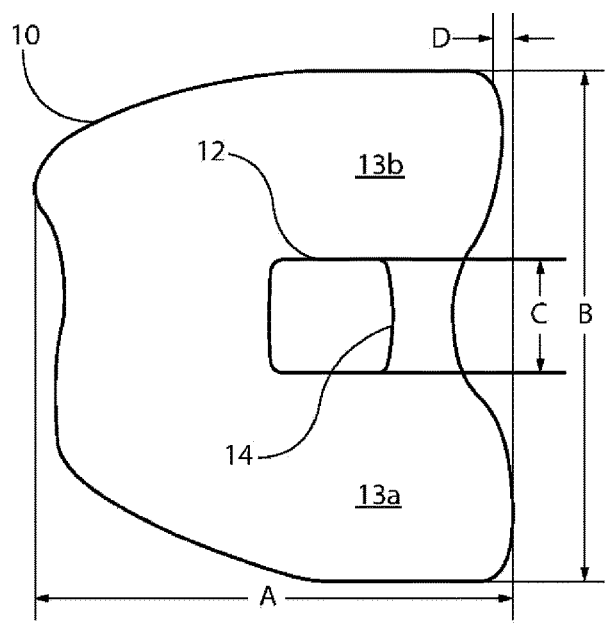
FIG. 1B is a bottom view of the femoral component of FIG. 1A.
Figure 2A:
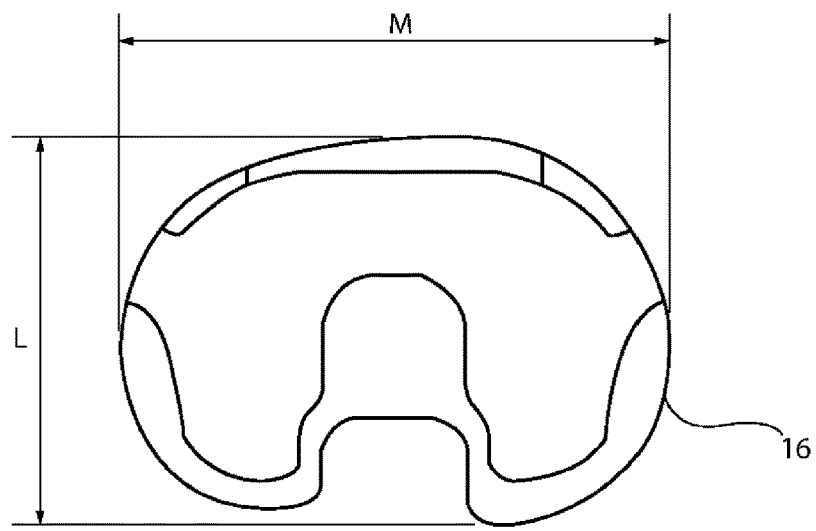
FIG. 2A is a top view of a tibial component for a knee joint prosthesis known by those of ordinary skill in the art.
Figure 2B:
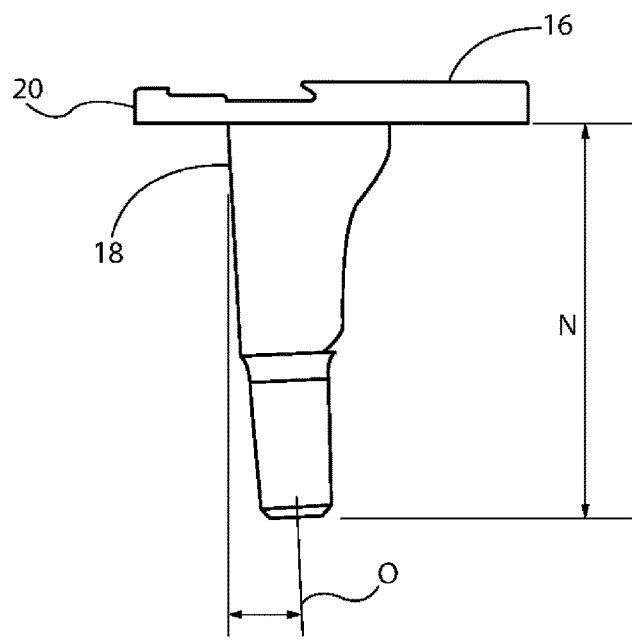
FIG. 2B is a side view of the tibial component of FIG. 2A.
Figure 3A:
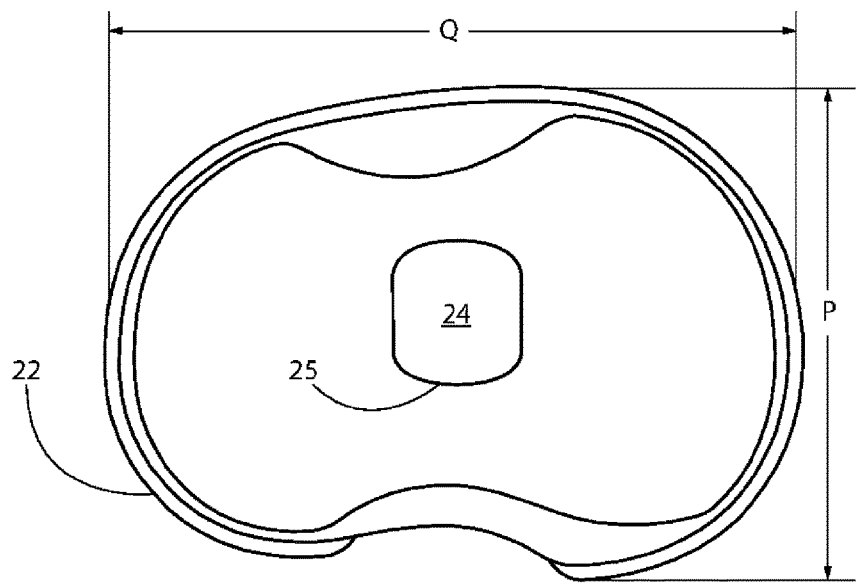
FIG. 3A is a top view of an articular insert for a knee joint prosthesis known by those of ordinary skill in the art.
Figure 3B:
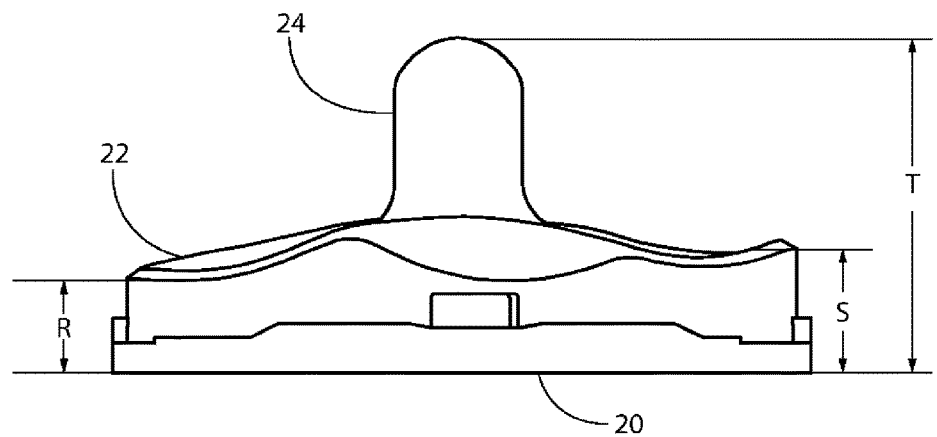
FIG. 3B is a front view of the articular insert of FIG. 3B mounted on the baseplate of a tibial component.
Figure 10A:
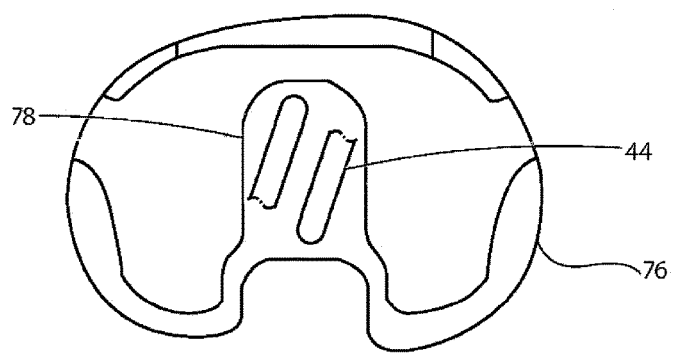
FIG. 10A is a top view of a tibial portion according to yet another embodiment of the present invention.
Figure 10C:
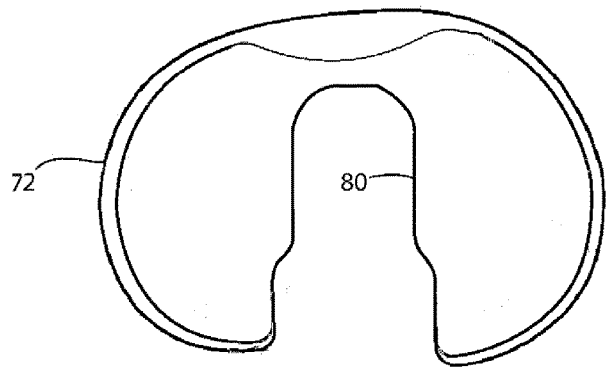
FIG. 10C is an articular insert that may be combined with the tibial portion of FIG. 10A.
Figure 10B:
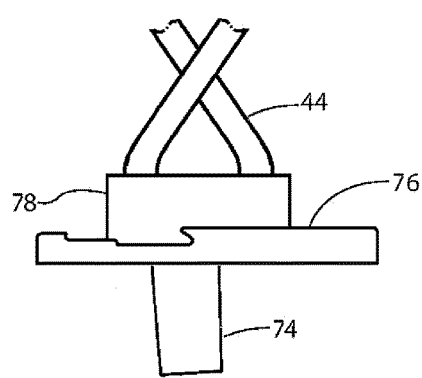
FIG. 10B is a side view of the tibial portion of FIG. 10A.

A particularly preferred embodiment of the present invention is illustrated in FIGS. 10A-10C. In the embodiment of FIGS. 10A-10C, the artificial ligament 44 is embedded, attached, and/or inserted in a raised platform section 78 of a tibial baseplate 76. A fastener 74 may extend from the bottom surface of the tibial baseplate 76. The fastener 74 may be attached to a rod, such as a typical rod 18 associated with a tibial component of a TKR, as illustrated in FIG. 2B. Any means known to those of skill in the art may be used to fasten the tibial portion 76 to a rod. For example, the fastener 74 may be in the form of a screw with corresponding threads provided in the rod or a Morse taper may be used to combine the components. This embodiment therefore allows for the selection of various rod lengths (identified as dimension N in FIG. 2B).

In order to insert an articular insert between the tibial portion 76 illustrated in FIGS. 10A and 10B and the femoral component of a TKR, the articular insert 72 may be provided with a cutout 80, as illustrated in FIG. 10C. The cutout 80 may have the same or a similar shape as the raised platform section 78. The cutout 80 therefore allows the articular insert 72 to be inserted from the anterior side of the tibial baseplate 76 after the artificial ligaments have been secured. The ligaments 44 attached, embedded, and/or inserted in the raised platform section 78 may be directly connected to a femoral component of a TKR or to a femoral portion of an ACL/PCL module, such as the femoral portion 40 illustrated in FIG. 7B.

The shape, size, and orientation of the upper and lower portions of the ACL/PCL module is not limited. For example both the upper and lower portion may be shaped like the lower portion 42 illustrated in FIG. 9A and the femoral component 50 may be provided with a groove similar to groove 61 of the articular insert 60. Such a construction may simplify manufacturing by reducing the number of different components. In another embodiment, rather than have a two-piece tibial baseplate, the lower portion may be a one-piece design, such as in the form of an articular insert similar to the embodiment illustrated in FIG. 5, with a different anchoring feature that allows attachment of the artificial ligaments to the lower portion. Preferably, in this embodiment, two artificial ligaments connect the standard articular insert and the modular femoral portion together, such that the attending physician may slide the entire insert into place during the surgical procedure. In another iteration, the artificial ligament may be anchored in the articular insert at one end, extend through a tunnel in the femoral component (not shown), return through the tibial component to an anchor at the other end. The type of fastening mechanism used to attach each portion of the module to the femoral component and articular insert or tibial component may also include any of one or more means known in the art for attachment. For example, the femoral portion of the module may use a Morse taper, a screw-in fastener, or both. Any combination and order of connecting the cord-like material between the two parts of the module may be acceptable, as long the result is a TKR having an artificial ACL and PCL.

The use of an ACL/PCL module in various embodiments of the present invention is preferable because not only does the module allow the individualized selection of a femoral component, tibial component, and articular insert for a patient who will undergo a TKR procedure, but it also provides a standard ACL/PCL module that may be used with any combination of components. For example, all of the femoral components made and sold by a manufacturer may include the same size gap 54 illustrated in FIG. 8 to accommodate a standard size femoral portion 40 of an ACL/PCL module, regardless of the other dimensions of the femoral component, for example dimensions A,B, and D-H in FIGS. 1A and 1B. The relative distance between the top of the tibial component and the bottom of the femoral component of the prosthetic knee is generally constant; therefore, the ligaments may have a constant length, regardless of the other dimensions of the components. Therefore, only a minor modification to an existing product line may be needed to incorporate an ACL/PCL module according to the present invention, and only a single or a limited number of modules may be provided to accommodate all of the various acceptable combinations and permutations of existing components. While it may be particularly advantageous to have only a single modular component size, it may be found that providing multiple sizes provides advantages, so the modular embodiment is not limited to only a single size embodiment.

While preferred embodiments of the invention have been shown and described herein, it will be understood that such embodiments are provided by way of example only. Numerous variations, changes, and substitutions may occur to those skilled in the art without departing from the spirit of the invention. Accordingly, it is intended that the appended claims cover all such variations that fall within the spirit and scope of the invention.

I claim:

1. A prosthetic knee comprising:
   a femoral component configured for fixation to the distal portion of a femur;
   a tibial component configured for fixation to the proximal portion of a tibia, the tibial component comprising an articular insert configured to be coupled to the tibial component, and
   an artificial ligament connecting the femoral component and the tibial component, the artificial ligament comprising an anterior cruciate ligament portion connecting an anterior anchor point on the tibial component to a posterior anchor point on the femoral component, and a posterior cruciate ligament portion connecting a posterior anchor point on the tibial component to an anterior anchor point on the femoral component,
   wherein the artificial ligament comprises a single continuous length of material in which the anterior cruciate ligament portion and the posterior cruciate ligament are connected to one another.

2. The prosthetic knee of claim 1 further comprising an ACL/PCL module attachable to the prosthetic knee, said ACL/PCL module comprising:
   at least one of a femoral portion configured to be coupled to the femoral component and a tibial portion configured to be coupled to at least one of the articular insert and the tibial component; and
   the artificial ligament connecting the femoral component and the tibial component.

3. The prosthetic knee of claim 2, wherein the tibial portion comprises an insert configured to be releasably coupled to the articular insert.

4. The prosthetic knee of claim 2, wherein the tibial portion comprises an insert configured to be releasably coupled to the tibial component.

5. The prosthetic knee of claim 2, wherein the femoral portion comprises an insert configured to be releasably coupled to the femoral component.

6. The prosthetic knee of claim 2, wherein each end of the single length of material is fastened to the tibial portion.

7. The prosthetic knee of claim 2, wherein each end of the single length of material is fastened to the femoral portion.

8. The prosthetic knee of claim 2, wherein the ends of the single length of material are attached to one another to form a continuous loop.

9. The prosthetic knee of claim 2, wherein the femoral portion of the module is configured to slidably engage the femoral component or the tibial portion of the module is configured to slidably engage the tibial component.

10. The prosthetic knee of claim 2, wherein the module is configured to be retained in engagement with the femoral component via a locking taper or retained in engagement with the tibial component via a locking taper.

11. The ACL/PCL module of claim 2, wherein the artificial ligament comprises at least one of polyethylene, carbon fiber, and PTFE.

12. The prosthetic knee of claim 1, wherein each end of the single length of material is fastened to the tibial component.

13. The prosthetic knee of claim 1, wherein each end of the single length of material is fastened to the femoral component.

14. The prosthetic knee of claim 1, wherein the artificial ligament comprises at least one of polyethylene, carbon fiber, and PTFE.

15. The prosthetic knee of claim 1, wherein the artificial ligament passes through a tunnel, bore or groove formed in the tibial component, and each end of the single length of material is fastened to the femoral component.

* * * * *